United States Patent [19]

Barnaby

[11] Patent Number: 4,566,311

[45] Date of Patent: Jan. 28, 1986

[54] MERCURY PUMP

[75] Inventor: Harold T. Barnaby, Duncanville, Tex.

[73] Assignee: Core Laboratories, Inc., Dallas, Tex.

[21] Appl. No.: 649,120

[22] Filed: Sep. 10, 1984

[51] Int. Cl.[4] ............................................. G01N 7/14
[52] U.S. Cl. ........................................... 73/19; 73/38
[58] Field of Search ................ 73/19, 38, 153; 175/50

[56] References Cited

U.S. PATENT DOCUMENTS

| | | | |
|---|---|---|---|
| 2,254,006 | 8/1941 | Exline | 73/38 |
| 2,296,852 | 9/1942 | Horner | 73/38 |
| 2,445,494 | 7/1948 | Redmond | 73/38 |
| 2,458,093 | 1/1949 | Muskat et al. | 73/153 |
| 2,679,159 | 5/1954 | Messer | 73/38 |
| 2,749,220 | 6/1956 | Rochon | 73/19 |
| 3,113,448 | 12/1963 | Hardway, Jr. et al. | 73/149 |
| 3,371,520 | 3/1968 | Sloane et al. | 73/38 |
| 3,494,188 | 2/1970 | Boatman, Jr. | 73/153 |

Primary Examiner—Stephen A. Kreitman
Attorney, Agent, or Firm—Lee C. Robinson, Jr.

[57] ABSTRACT

A mercury pump for analyzing geological core samples has a vertically oriented cylindrical cavity in which a lower portion forms a mercury displacement chamber and an upper portion in axial alignment with it forms a sample chamber. A pressure transducer, e.g., a strain gauge or solid-state sensor, in communication with the sample chamber produces an electrical pressure signal. A screw ball jack urges a synthetic-resin piston upwards in the displacement section to push the mercury into the sample chamber. The displacement of the mercury is sensed by an electronic encoder coupled to the hand crank of the jack, and provides data regarding both the direction and the amount of piston displacement. A microprocessor-controlled volume-measuring device has inputs connected to the encoder, and automatically provides core sample data, in response to the signals from the encoder, at the end of a core test run.

10 Claims, 4 Drawing Figures

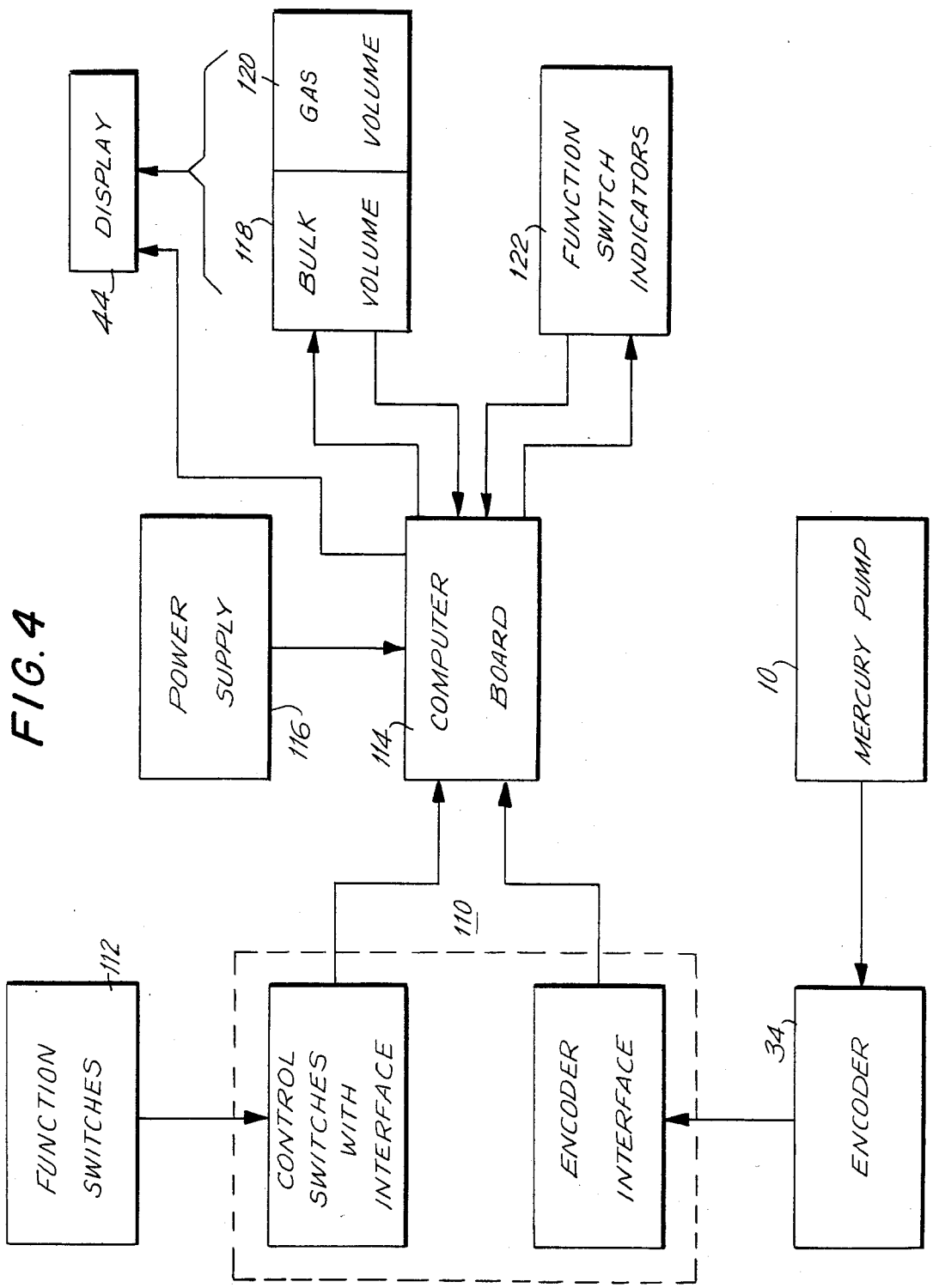

MERCURY PUMP

The present invention relates to tools and techniques for evaluating mineral deposits, especially in connection with the exploration for petroleum. The invention is more particularly directed to a so-called mercury pump in which mercury is forced, under pressure, into microscopic pores and apertures in a geological core sample and which provides data about the gas content of the core sample.

A currently-used mercury pump is described, for example, in commonly-assigned U.S. Pat. No. 2,296,852.

It has been discovered that a relationship exists between the ratio of free gas to oil in a rock layer on the one hand, and on the other hand the probable gas to oil ratio under which a well in that rock layer will produce. Generally speaking, the higher the free gas to oil ratio, the higher will be the gas to oil ratio of the flowing well. Because at least a minimum amount of gas should be produced with each barrel of oil to secure the best yield, the gas content of a rock core sample is an important index, and is valuable in the exploration of oil.

A mercury pump is used to test rock core samples for their gas content. This is done by compressing the gas in the core sample with a non-compressible liquid, usually mercury, in which the core sample is immersed. The mercury is forced into the pores in the sample to compress the gas, and the volume of the liquid required to do this is measured. The readings thus obtained can be readily translated into the percent gas per unit volume of the rock from which the core has been taken; this, of course, translates into a characteristic of the rock itself, from which the probability of profitable oil exploitation can be deduced. In a typical mercury pump, there is a sample chamber having a suitable air vent at its top and an inlet at its bottom through which the incompressible liquid is flooded into the chamber from a displacement chamber. Initially, the device is calibrated by flooding the empty chamber with mercury, and reading the volume on a vernier scale. Then, the mercury is withdrawn back into the mercury displacement chamber, and a core sample is inserted into the sample chamber. After this, mercury is again flooded into the sample chamber, at atmospheric pressure, until the level of mercury appears at an open port on the cover of the mercury pump. At this time, the volume of displaced mercury is read from the vernier scale, and the difference between the two readings is equal to the overall volume of the core sample. Then, a pressure fitting is closed to seal the open port, and mercury is again displaced into the sample chamber. The mercury is subjected to a pressure of, for example, 50 atmospheres, which causes the mercury to penetrate the microscopic cracks, crevices, and pores of the core sample and to compress and supplant the gas present in it until the gas occupies only 1/50 of the volume that it would occupy at one atmosphere. The volume of the liquid thus entering the pores of the sample is measured, and this volume can be corrected upwards by 2% to compensate for the residual volume of gas at 50 atmospheres.

From this reading, and from the previous reading giving the volume of the core sample itself, there is obtained the fraction of the core volume that is occupied by free gas. In addition, the rate at which the mercury enters the core sample's pores and other microscopic spaces under 50 atmospheres of pressure can also be measured as an indication of the permeability of the core sample.

In the apparatus for carrying out this technique, the sample chamber is generally connected to a separate displacement chamber. The sample chamber is closed at its top by a suitable cover which may be bolted in place after the sample is in place in the chamber. The port or vent can be in the cover, and the pressure fitting can be a simple needle valve. Generally, the displacement chamber has a piston or plunger of a predetermined cross-sectional area which is screw-driven into the displacement chamber by means of a hand wheel. The number of turns of the hand wheel corresponds to the volume of mercury displaced, and this volume is measured by noting the markings of a vernier scale on the hand crank. Also, during a measurement, the actual pressure is noted manually by observing a conventional pressure gauge attached to the displacement chamber.

Because current and previously-used mercury pumps are formed of separate displacement and sample chambers, alignment can become a problem. Also, the use of a conventional pressure gauge and the use of manually-read vernier scales can often produce human errors in measurements. Furthermore, this conventional mercury pump does not lend itself readily to automation, nor does it accommodate the automatic, digitized calculation of the core sample's geological parameters.

It is a desired object of this invention to provide a mercury pump which avoids the shortcomings of the previously-proposed mercury pumps.

It is another object of this invention to provide a mercury pump which has a unitary sample and displacement chamber, thereby achieving a simplified, more reliable design.

It is yet another object of this invention to provide a mercury pump in which the displaced volume of mercury or other incompressible liquid is measured automatically, and without resort to an operator's reading of a vernier scale or the like, thereby avoiding a major source of human error.

It is a further object of this invention to provide a mercury pump in which the displacement of mercury or other compressible liquid can be determined with an accuracy that is an order of magnitude better than with previously-proposed mercury pumps.

It is still another object of this invention to provide a mercury pump in which the mercury pressure during a measurement is sensed electronically by means of a strain gauge, solid-state transducer, or the like.

It is a yet further object of this invention to provide a drive for displacing the piston of the mercury pump with a drive mechanism that is extremely durable and is relatively friction-free.

The above and other desired objects of this invention are realized with a mercury pump according to this invention, which is highly suitable for the analysis of geological core samples. In accordance with several desired aspects of this invention, the mercury pump has a vertically oriented cylindrical cavity in which a lower portion forms a mercury displacement chamber and a upper portion in axial alignment therewith forms a sample chamber. A pressure transducer, such as a strain gauge or solid-state sensor, communicates with the sample chamber and produces an electrical pressure signal. A screw ball jack urges a synthetic-resin piston upwards in the displacement section to push mercury (or other incompressible liquid) therefrom into the sample chamber. The displacement of the mercury is sensed by an electronic encoder coupled to the hand crank of the jack, and this provides the data relating to both the direction and the amount of piston displacement. Favorably, the encoder is accurate to within .001 cubic centimeters displacement. A microprocessor-controlled volume measuring device has inputs connected to the encoder, and automatically calculates core sample data, in response to the signals from the encoder and from the pressure transducer, at the end of a core test run. In several favorable embodiments, the piston of the mercury pump displacement chamber section is formed of a durable, mercury-resistant synthetic resin material, for example, nylon.

The above and many other objects, features and advantages of this invention will become apparent from the ensuing detailed description of an exemplary preferred embodiment, which description is to be read in connection with the accompanying drawings, in which:

FIG. 4 is a circuit block diagram showing the overall operation of the mercury pump and its associated electronics.

Figure 1:
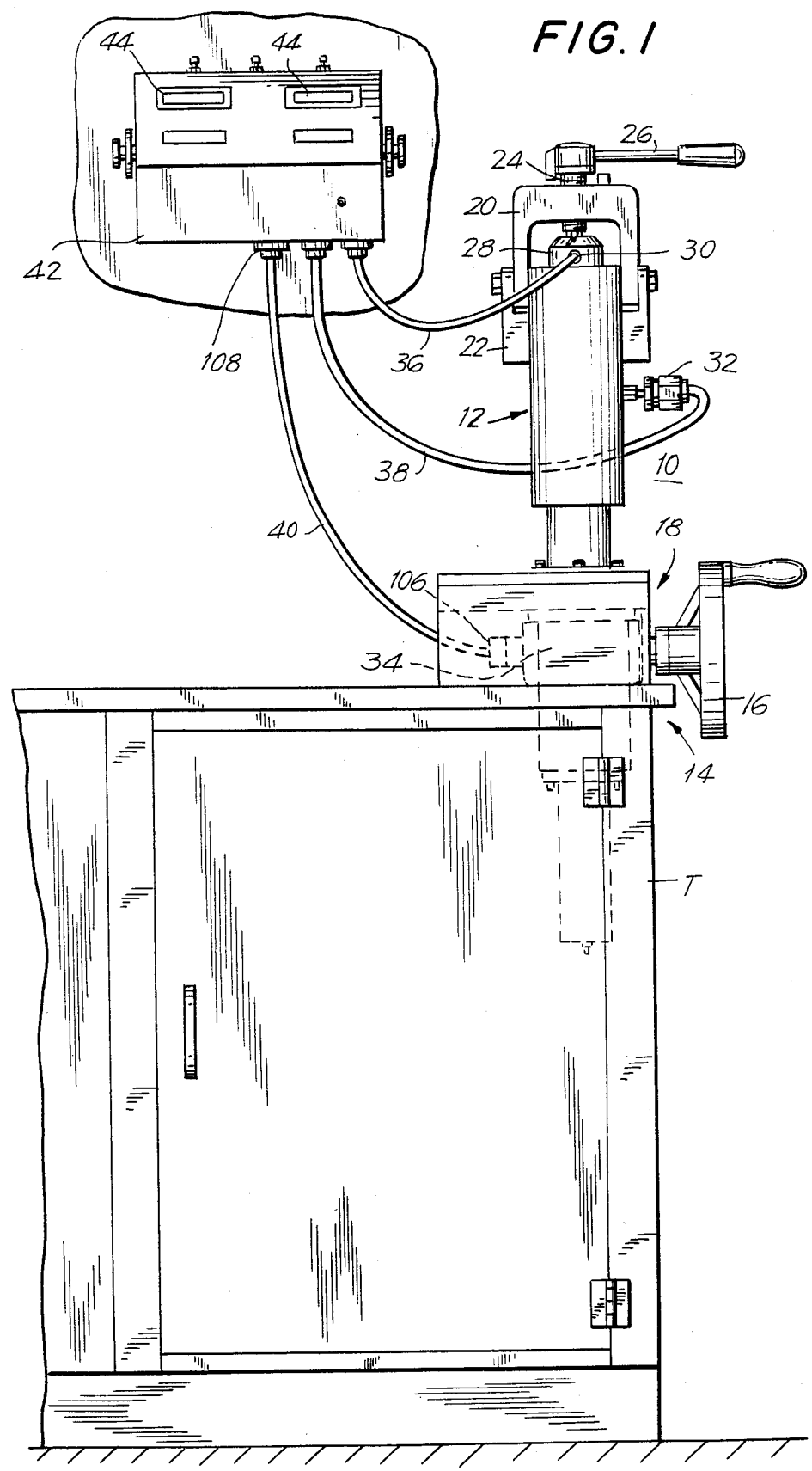
FIG. 1 is a front elevational view of a favorable embodiment of the mercury pump of this invention, shown mounted on a typical laboratory bench.
Figure 2:
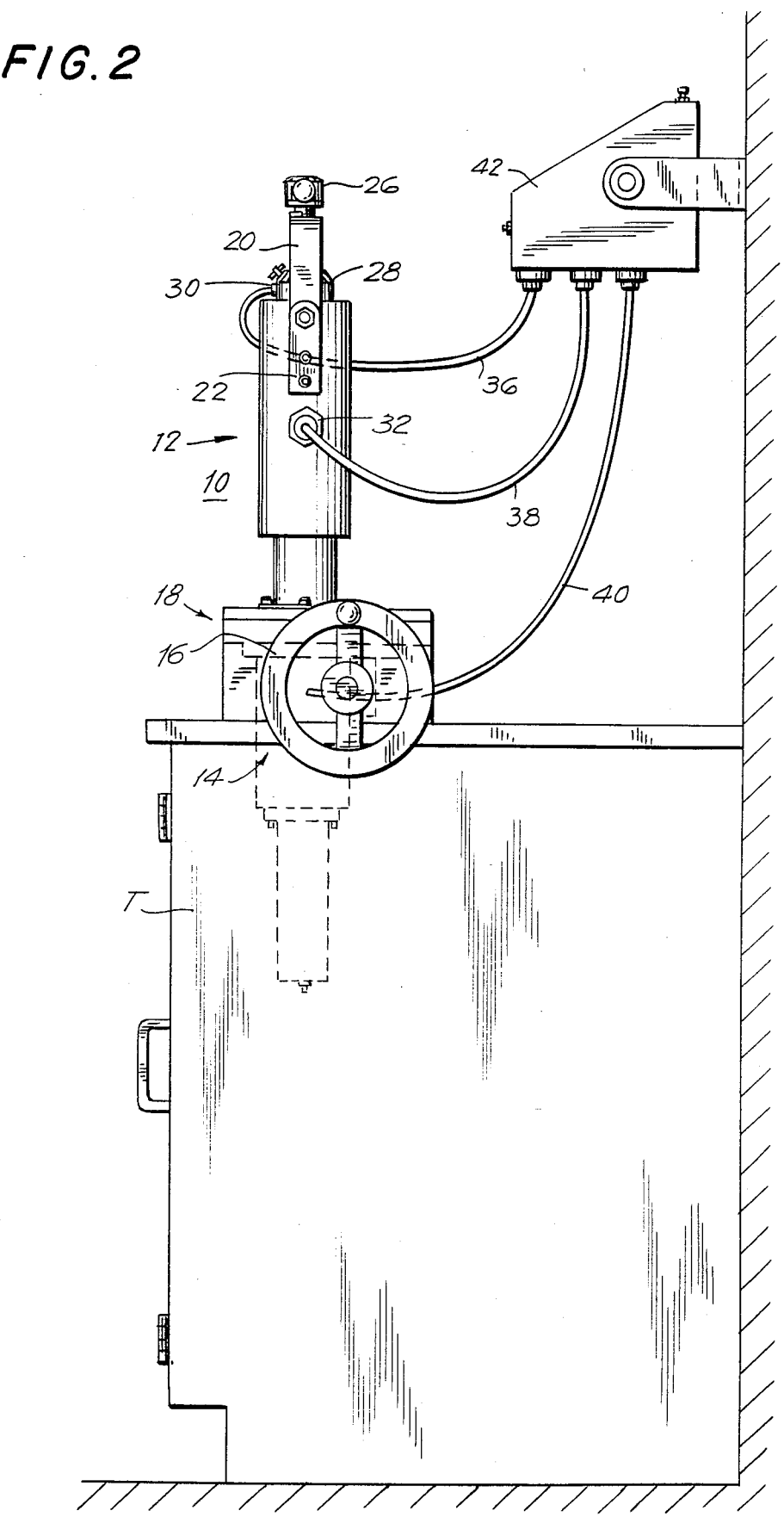
FIG. 2 is a side elevational view of this embodiment of the mercury pump.
Figure 3:
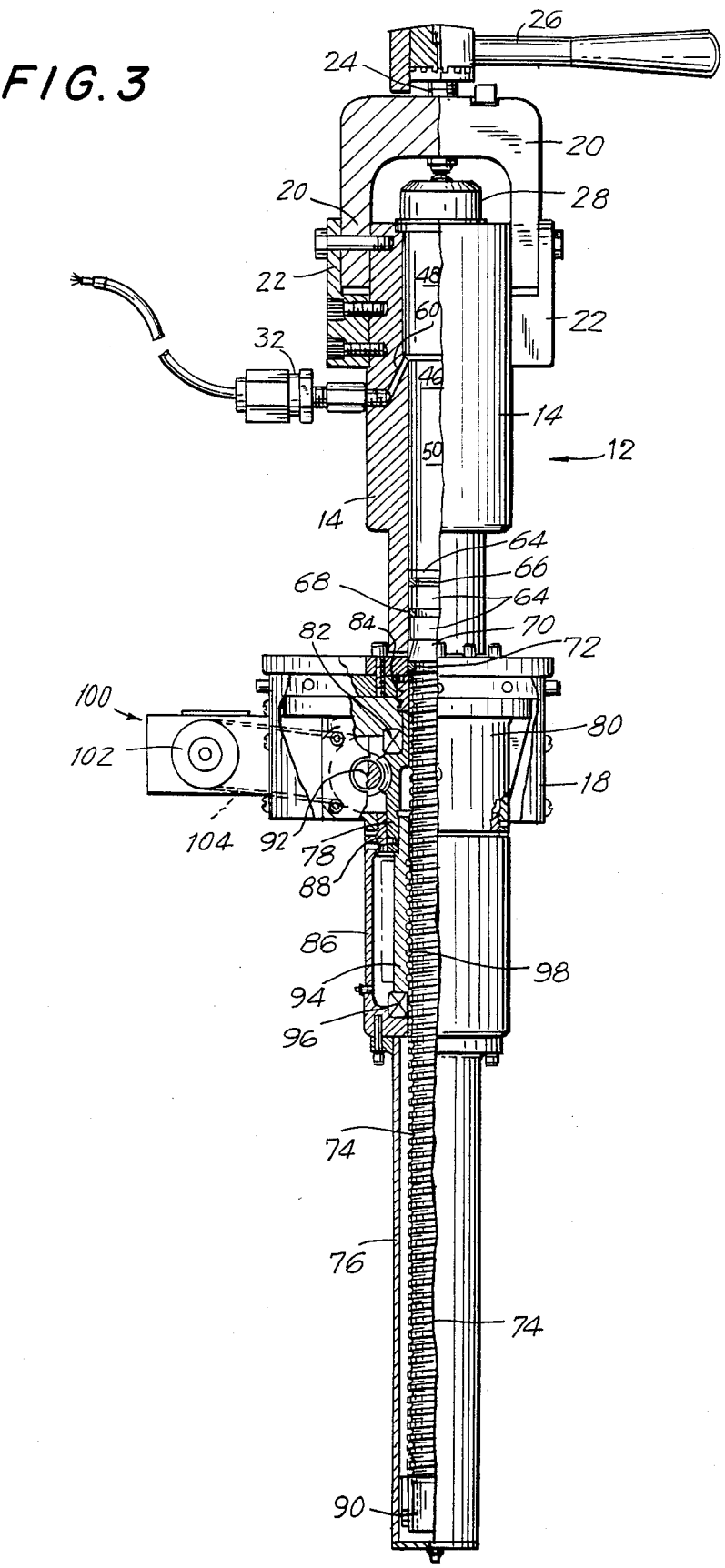
FIG. 3 is another elevational view, partly in section, showing the construction of this embodiment.

With reference to the accompanying drawings, and initially to FIGS. 1-3 thereof, the mercury pump 10 of this invention is formed of a pump body 12 mounted atop a screw ball jack 14 having a hand wheel 16 and an enclosure 18. The mercury pump 10 can be mounted on a suitable bench or table T. On the pump body 12 a U-shaped yoke 20 is hingedly supported on a yoke bracket 22. A self-centering/locking pull-down screw 24 is threadably mounted on the yoke 20 and has a handle 26 for turning to tighten or loosen the screw 24. This screw 24 holds down a cap 28 which seals off the pump body 12 at an open top thereof. A level sensor 30 disposed at the top of the body 12 provides an indication when the pump body 12 is filled with mercury. Also, a pressure sensor 32, which can be a strain gauge or a solid-state pressure transducer, communicates through a channel with the interior of the pump body 12, and provides an electrical output value corresponding to the pressure within the pump body 12.

A counter/encoder 34 is mounted within the enclosure 18 and is rotationally coupled to the hand crank 16. This counter/encoder provides one thousand counts per turn of the hand crank 16, with each count corresponding to 0.001 cubic centimeters displacement of mercury within the pump body 12. Cables 36 and 38 lead from the level sensor and pressure sensor, respectively, and a multi-lead cable 40 leads from the counter/encoder 34. These cables 36, 38, 40 are coupled to an electronic processor 42 having liquid crystal displays 44 which provide visible readings of the output calculated values corresponding, for example, to the measured gas content of a core sample.

As is perhaps better shown in FIG. 3, the pump 12 has a vertical cylindrical cavity 46, an upper part of which forms a core sample chamber 48 into which a geological core sample is inserted, and a lower part of which forms a mercury displacement chamber 50. A channel 60 leads from the base of the core sample chamber 48 to the pressure sensor 32. The core sample chamber 48 has a slightly greater diameter than the mercury displacement chamber 50.

Within the displacement chamber 50, a piston is fitted. This piston is formed of a piston body 64, preferably formed of a nylon or another suitable mercury-resistant polymer, a piston seal 66 disposed in an annular circumferential cutout on the piston body 64, a felt oiler 68 disposed in another annular cutout on the piston body 64, and a lower gland 70 at the base of the piston body 64. An O-ring seal 72 is disposed at the base of the lower gland 70.

The piston is displaced upwards and downwards in the cylindrical displacement chamber 50 by means of the screw ball jack 14, the details of which are now described. This jack 14 has a vertical threaded lifting screw 74 extending axially, and a cylindrical screw cover 76 disposed over the lower portion thereof. Within the enclosure 18 there is a generally cylindrical drive sleeve 78 mounted for rotation within a drive housing 80 with a bearing 82 permitting mutual rotation thereof. A bushing 84 is disposed between the drive sleeve 78 and the pump body 12. A housing extension 86, of generally cylindrical form, is coupled from the housing 80 to the screw cover 76 by means of an adapter 88.

At the lower end of the lifting screw 74, a torque nut 90 holds the screw 74 to the screw cover 76 to hold the lifting screw 74 against rotation.

An input worm shaft 92, coupled to the hand wheel 16, threadedly engages the drive sleeve 78 to rotate the latter. A ball nut 94 is mounted on the drive sleeve 78 and rotates with it. The ball nut 94 is separated by a bearing 96 from the housing extension 86. A plurality of spheroids or balls 98 ride in the threads between the nut 94 and the screw 76 to provide a recirculating-ball type of screw drive which is of extremely low friction and requires very little in the way of lubrication or maintenance. The ball nut 94, the balls 98, and the lifting screw 74 together define a return-ball race lifting mechanism.

As shown in both FIGS. 2 and 3, the counter/encoder 34 includes an indexing mechanism 100 having a timing gear 102 thereon which is coupled, by means of a timing belt 104, to the input worm shaft 92. Verniers 106 are also provided on the indexing mechanism to provide a visual indication of mercury displacement. The indexing mechanism 100 is of a known type, for example, magnetic or electro-optical, providing one thousand counts per revolution of the input worm shaft 92, and also providing an indication of the direction of rotation thereof. A plurality of leads extend through the cable 40 from the counter/encoder 34 to a multi-pin connector 108 which can be plugged into a corresponding socket on the electronic processor 42.

The operation of this device can be understood with reference to the diagram of FIG. 4. First, during the testing run for a particular core sample in the mercury pump 10, the encoder 34 provides count and direction information to an interface circuit 110, while function switches 112, having been previously selected, also provide data to the interface 110. The data from the interface 110 are provided to suitable inputs of a computer board 114, which is powered by an appropriate power supply 116, for example, regulated 5 volts DC. In the computer board 114, bulk volume counter 118 (i.e.. the overall volume of the core sample), and gas volume counter 120 (i.e., the difference between the mercury volume readings at one atmosphere and 50 atmospheres), are employed, and the values corresponding to their contents (i.e., bulk volume and gas volume) are displayed on the LCD display 44. Then, with these data from the counters 118 and 120, the computer board 114 calculates the effective relative gas content of the core sample, and this value is also furnished to the display 44. During the core sample test run and during the computation phase, function switch indicators 122 are actuated by the computer board 114 to indicate the various operating phases to an operator monitoring or overseeing the mercury pump operation. The counters 118, 120 are separately operative during respective phases of the core sample testing process.

With the mercury pump arrangement as described hereinabove, the data relating to core sample geological properties are displayed on a large digital meter for high visibility, and these data are also retained in digital code form for transmission and for use by other computer systems. The mercury pump and electronics processor described hereinabove can convert the raw data into any number of engineering parameters, depending upon the application required. Further, this arrangement has the ability to correct the data for volumetric errors due top manufacturing tolerance, for example. The data measured for each phase of a test run are maintained on the visual display 44 until that particular test run is completed, or the data are intentionally cancelled.

Throughout the description, and in the art generally, the term "mercury pump" is used generally in connection with this type of core sample analysis device, even though any suitable incompressible liquid could be used instead of mercury. Mercury is preferred, however, because of its high density and because its electrical conductivity makes level sensing relatively easy. Also, while the vertical orientation shown in the drawings is preferred, it is clear that a diagonal or horizontal orientation could also be employed, in suitable circumstances. Still further, although a manual hand wheel is employed in this embodiment, it is quite clear that an electrical motor could be employed with suitable modifications to the mechanism.

While the invention has been described hereinabove with reference to a single preferred embodiment, it is evident that many modifications and variations thereof would present themselves to persons of ordinary skill in the art without departure from the scope and spirit of this invention, as defined in the appended claims.

What is claimed is:

1. Mercury pump for testing the gas content of a geological core sample, comprising
a pump body having a vertically oriented chamber therein, a lower portion of which defines a mercury displacement chamber section and an upper part of which forms a sample chamber section into which the core sample can be inserted;
a removably securable sample chamber cap for sealing the top of said pump body;
a pressure transducer disposed in communication with the interior of said chamber and providing an output pressure signal;
a piston disposed in said mercury displacement chamber section and arranged to move vertically to displace mercury in said section;
drive means for driving said piston vertically in said mercury displacement chamber section, the drive means including an elongated vertical drive screw having said piston mounted on an upper end thereof; a drive housing; a hand wheel; a threaded, horizontally disposed input worm shaft coupled to said hand wheel; a drive sleeve mounted in said drive housing about said screw and rotationally driven by said input worm shaft; a threaded-race ball nut disposed about said screw and connected to said drive sleeve; a plurality of balls disposed in the threaded race of said ball nut defining therewith a return-ball race lifting mechanism for said vertical drive screw; and means holding said drive screw against rotation relative to said drive housing;
a displacement encoder rotationally coupled to said input worm shaft providing data indicating the direction of rotation of said worm shaft and a count for each predetermined increment of rotation thereof, said encoder providing on the order of one count for each one-thousandth of a cubic centimeter of displacement of said piston; and
microprocessor-controlled volume measuring means having inputs coupled to said displacement encoder and to said pressure transducer for processing data determined from the counts from said displacement encoder to provide data relating to the gas content of said core sample.

2. Mercury pump according to claim 1, further comprising a yoke mechanism for holding said sample chamber cap on said pump body, including a yoke support bracket on said pump body, a yoke swingably mounted on said yoke support bracket, and a hold down screw-type locking and centering device for engaging said cap when said yoke is swung into place over said cap.

3. Mercury pump according to claim 1, wherein said mercury displacement chamber section is a cylindrical cavity of a first predetermined diameter and said sample chamber section is a substantially cylindrical cavity coaxial with said mercury displacement chamber section and of a second, larger diameter.

4. Mercury pump according to claim 1, wherein said piston is formed of a synthetic resin material.

5. Mercury pump according to claim 4, wherein said piston is formed of nylon.

6. Mercury pump for testing the gas content of a geological core sample, comprising
a pump body having a vertically oriented mercury displacement chamber therein, formed of a mercury displacement chamber section and a sample chamber section in communication with the mercury displacement chamber section and into which the core sample can be inserted, said chamber sections being axially aligned;
a removably securable sample chamber cap for sealing the top of said pump body;
a pressure sensor disposed in communication with the interior of said chamber;
a piston disposed in said mercury displacement chamber section and arranged to move vertically to displace mercury in said mercury displacement chamber section;
drive means for driving said piston vertically in said mercury displacement chamber section, the drive means including an elongated vertical drive screw having said piston mounted on an upper end thereof; a drive housing; a hand wheel; a threaded, horizontally disposed input worm shaft coupled to said hand wheel; a drive sleeve mounted in said drive housing about said screw and rotationally driven by said input worm shaft; a threaded-race ball nut disposed about said screw and connected to said drive sleeve; a plurality of balls disposed in the threaded race of said ball nut defining therewith a return-ball race lifting mechanism for said vertical drive screw; and means holding said drive screw against rotation relative to said drive housing;

a displacement encoder rotationally coupled to said input worm shaft providing data indicating the direction of rotation of said worm shaft and a count for each predetermined increment of rotation thereof, said encoder providing on the order of one count for each one-thousandth of a cubic centimeter of displacement of said piston; and microprocessor-controlled volume measuring means having inputs coupled to said displacement encoder and to said pressure transducer for processing data determined from the counts from said displacement encoder to provide data relating to the gas content of said core sample.

7. Mercury pump for testing the gas content of a geological core sample, comprising a pump body having a unitary mercury displacement-/sample chamber therein, a lower portion of which defines a mercury displacement chamber section and an upper part of which forms a sample chamber section into which the core sample can be inserted;

a removably securable sample chamber cap for sealing the top of said pump body;

a pressure transducer disposed in communication with the interior of said chamber and providing an output pressure signal;

a piston disposed in said mercury displacement chamber section and arranged to move vertically to displace mercury in said section;

drive means for driving said piston vertically in said mercury displacement chamber section, the drive means including a ball screw jack having a screw shaft with said piston mounted on an upper end thereof; a drive housing; a hand wheel; an input shaft coupled to said hand wheel; and means coupled to said screw shaft for driving the same axially upon rotation of said input shaft;

a displacement encoder rotationally coupled to said input shaft providing data indicating the direction of rotation of said input shaft and a count for each predetermined increment of rotation thereof, said encoder providing on the order of one count for each one-thousandth of a cubic centimeter of displacement of said piston; and microprocessor-controlled volume measuring means having inputs coupled to said displacement encoder and to said pressure transducer for processing data determined from the counts from said displacement encoder to provide data relating to the gas content of said core sample, said microprocessor-controlled volume measuring means including first and second counter means for processing said counts from said encoder, each separately operative during respective phases of a process for measuring the gas content of said core sample.

8. Mercury pump for testing the gas content of a geological core sample, comprising a pump body having a unitary mercury displacement-/sample chamber therein, one portion of which defines a mercury displacement chamber section and another portion of which forms a sample chamber section into which the core sample can be inserted;

a removably securable sample chamber cap for sealing the top of said pump body;

a solid-state pressure transducer disposed in communication with the interior of said chamber and providing an output pressure signal;

a piston disposed in said mercury displacement chamber section and arranged to displace mercury in said section;

drive means for driving said piston vertically in said mercury displacement chamber section, the drive means including a ball screw jack having a screw shaft with said piston mounted on a upper end thereof; a hand wheel; an input shaft coupled to said hand wheel; and means coupled to said screw shaft for driving the same axially upon rotation of said input shaft;

a displacement encoder rotationally coupled to said input shaft providing data indicating the direction of rotation of said input shaft and a count for each predetermined increment of rotation thereof, said encoder providing on the order of one count for each one-thousandth of a cubic centimeter of displacement of said piston; and microprocessor-controlled volume measuring means having inputs coupled to said displacement encoder and to said solid-state pressure transducer for processing data determined from the counts from said displacement encoder to provide data relating to the gas content of said core sample.

9. Mercury pump for testing the gas content of a geological core sample, comprising a pump body having a unitary mercury displacement-/sample chamber therein, one portion of which defines a mercury displacement chamber section and another portion of which forms a sample chamber section into which the core sample can be inserted;

a removably securable sample chamber cap for sealing the top of said pump body;

a strain-gauge pressure transducer disposed in communication with the interior of said chamber and providing an output pressure signal;

a piston disposed in said mercury displacement chamber section and arranged to move vertically to displace mercury in said section;

drive means for driving said piston vertically in said mercury displacement chamber section, the drive means including a ball screw jack having a screw shaft with said piston mounted on an upper end thereof; a hand wheel; an input shaft coupled to said hand wheel; and means coupled to said screw shaft for driving the same axially upon rotation of said input shaft;

a displacement encoder rotationally coupled to said input shaft providing data indicating the direction of rotation of said input shaft and a count for each predetermined increment of rotation thereof, said encoder providing on the order of one count for each one-thousandth of a cubic centimeter of displacement of said piston; and microprocessor-controlled volume measuring means having inputs coupled to said displacement encoder and to said pressure transducer for processing data determined from the counts from said displacement encoder to provide data relating to the gas content of said core sample.

10. Mercury pump for testing the gas content of a geological core sample, comprising a pump body having a unitary mercury displacement-/sample chamber therein, one portion of which defines a mercury displacement chamber section and another portion of which forms a sample chamber section into which the core sample can be inserted;

a removably securable sample chamber cap for sealing the top of said pump body;

a pressure sensor disposed in communication with the interior of said chamber;

a piston disposed in said mercury displacement chamber section and arranged to displace mercury in said section;

drive means for driving said piston vertically in said mercury displacement chamber section, the drive means including a ball screw jack having a screw shaft with said piston mounted on an upper end thereof; a hand wheel; an input shaft coupled to said hand wheel; and means coupled to said screw shaft for driving the same axially upon rotation of said input shaft;

a displacement encoder rotationally coupled to said input shaft providing data indicating the direction of rotation of said input shaft and a count for each predetermined increment of rotation thereof, said encoder providing on the order of one count for each one-thousandth of a cubic centimeter of displacement of said piston; and microprocessor-controlled volume measuring means having an input coupled to said displacement encoder for producing data, determined from the counts from said displacement encoder, relating to the gas content of said core sample.

* * * * *